United States Patent [19]

Krzyzek et al.

[11] Patent Number: 5,384,253
[45] Date of Patent: Jan. 24, 1995

[54] GENETIC TRANSFORMATION OF MAIZE CELLS BY ELECTROPORATION OF CELLS PRETREATED WITH PECTIN DEGRADING ENZYMES

[75] Inventors: Richard A. Krzyzek, Edina; Cheryl R. M. Laursen, St. Paul; Paul C. Anderson, Minneapolis, all of Minn.

[73] Assignee: DeKalb Genetics Corporation, DeKalb, Ill.

[21] Appl. No.: 635,279

[22] Filed: Dec. 28, 1990

[51] Int. Cl.$^6$ .................. C12N 15/00; C12N 15/05
[52] U.S. Cl. ......................... 435/172.3; 435/240.47; 435/240.49; 435/240.50; 435/240.46; 800/205; 935/67
[58] Field of Search .......... 435/240.4, 240.45, 240.49, 435/172.1, 172.3, 240.46

[56] References Cited

FOREIGN PATENT DOCUMENTS 290395 11/1988 European Pat. Off. .
292435A1 11/1988 European Pat. Off. .

OTHER PUBLICATIONS

C. Rhodes, "Plant Regeneration from Protoplasts Isolated from Embryogenic Maize Cell Cultures", *Bio/Technology*, 6:56–60 (1988).
S. Morocz et al., "Two Approaches to Rendering *Zea mays* L. Applicable to Tissue Culture Manipulations", *Abstract VIIth International Congress on Plant Tissue and Cell Culture*, Amsterdam A1–102, Abstract No. 209, p. 190 (1990).
I. Potrykus, *Biotechnology*, 535, 2 (1990).
R. A. Dekeyser et al., *Plant Cell*, 2, 591 (1990).
G. Donn et al., *Abstracts VIIth International Congress on Plant Tissue and Cell Culture*, Amsterdam A2–38 (1990).
I. Potrykus, *Physiologia Plantarum*, 79, 125 (1990).
K. Lindsey et al., *Physiologia Plantarum*, 79 168 (1990).
K. Lindsey et al., *Plant Cell Reports*, 8, 71 (1989).
J. Lee et al., *Korean J. Genetics*, 11, 65 (1989).
Y. Huang et al., *Plant Cell, Tissue and Organ Culture*, 18, 281 (1989).
K. Shimamoto et al., *Nature*, 338, 274 (1989).
H. Jones et al., *Plant Mol. Biol.*, 13, 503 (1989).
M. Horn et al., *Plant Cell Reports* 7, 469 (1988).
K. Schimamoto et al., *International Soc'y for Plant Molec. Biol.*, 2nd International Congress, Jerusalem (1988).
C. Rhodes et al., *Science*, 240, 204 (1988).
K. Weising et al., *Annu. Rev. Genet.*, 22, 421 (1988).
H. Yang et al., *Plant Cell Reports*, 7, 421 (1988).
K. Shigekawa et al., *BioTechniques*, 6, 742, (1988).
K. Lindsey et al., *Plant Molecular Biol.*, 10, 43 (1987).
E. Cocking et al., *Science*, 236, 1259 (1987).
H. Jones et al., *Oxford Surveys of Plant Molecular & Cell Biol.*, 4, 347 (1987).
H. Morikawa et al., *Gene*, 121 (1986).
M. Fromm et al., *Nature*, 319, 791 (1986).
M. Fromm et al., *PNAS USA*, 82, 5824 (1985).
H. Potter et al., *PNAS USA*, 81, 7161 (1984).

*Primary Examiner*—Gary Benzion
*Attorney, Agent, or Firm*—Warren D. Woessner

[57] ABSTRACT

The present invention provides a method to increase the susceptibility of cultured *Zea mays* cells to stable transformation with recombinant DNA via electroporation, by pretreating the *Zea mays* cells with certain pectin-degrading enzymes, so that the cells retain their ability to regenerate fertile, transgenic *Zea mays* plants containing the DNA which is also heritable.

21 Claims, 3 Drawing Sheets

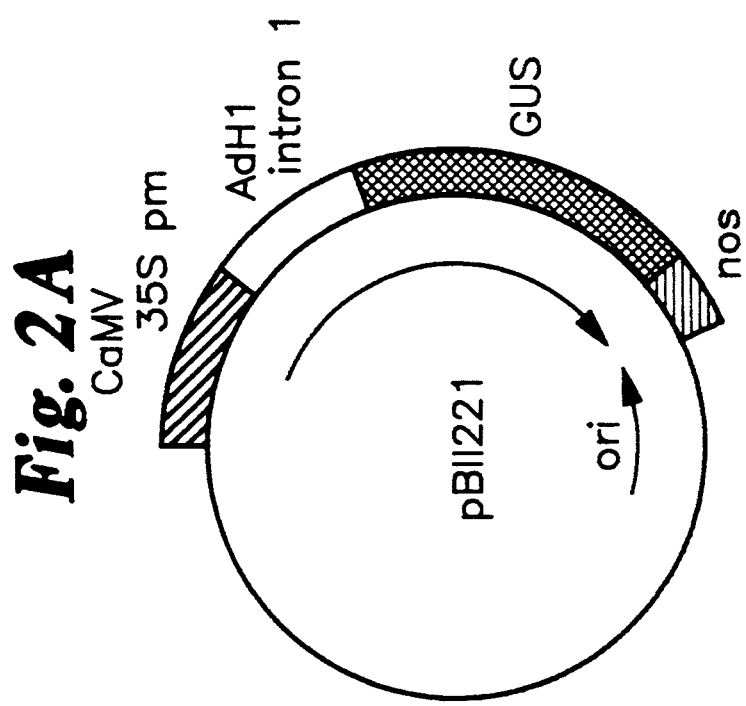
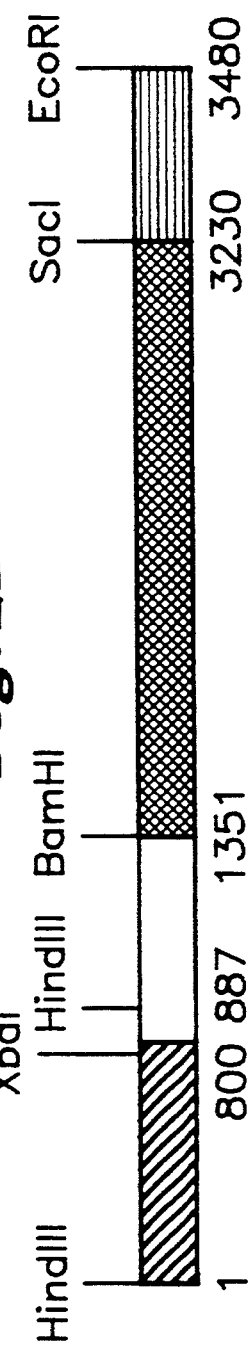
Fig. 2A
Fig. 2B

GENETIC TRANSFORMATION OF MAIZE CELLS BY ELECTROPORATION OF CELLS PRETREATED WITH PECTIN DEGRADING ENZYMES

FIELD OF THE INVENTION

This invention relates to producing transgenic corn cells via electroporation which are capable of regeneration to yield fertile transgenic corn plants.

BACKGROUND OF THE INVENTION

Genetic engineering of plants, which entails the isolation and manipulation of genetic material (usually in the form of DNA or RNA) and the subsequent introduction of that genetic material into a plant or plant cells, offers considerable promise to modern agriculture and plant breeding. Beneficial traits such as increased crop food values, higher yields, feed value, reduced production costs, pest resistance, stress tolerance, drought resistance as well as the production of pharmaceuticals, and other useful chemicals are all potentially achievable through genetic engineering techniques.

Once a gene has been identified and synthesized or cloned, and engineered, it is still necessary to integrate it into the genome of a plant of interest so that it is stably inherited by progeny of the transformed plant. Transient transformation leads to loss of the introduced DNA and is of little use in generating transgenic plants. Stable transformation involves the chromosomal integration of functional genetic sequences so that the integrated sequences are passed on to and present in the progeny of the transgenic plants. As referred to herein, chromosomal integration includes incorporation into plastid chromosomes. Genes incorporated into plastid chromosomes will display maternal inheritance. In order to produce transgenic corn plants, stably transformed cells must also be capable of giving rise to fertile transgenic plants. In contrast, transient transformation leads to the eventual loss of the introduced DNA and is of little use in generating transgenic plants. However, it is important in optimizing some conditions involved in stable transformation and evaluating gene expression.

Electroporation has been used to introduce foreign DNA into a number of plant species. This has almost exclusively been done using protoplasts as the DNA recipient. See M. E. Fromm et al., *Nature*, 319, 791 (1986); H. Jones et al., *Plant Mol. Biol.*, 13, 501 (1989) and H. Yang et al., *Plant Cell Reports*, 7, 421 (1988). However, this approach has encountered difficulties with many plant species. In general, monocot protoplasts are more difficult to generate and manipulate than are protoplasts from dicots. Monocot protoplasts can be isolated and kept viable but rarely reform normal cell walls and divide, in contrast to dicots which in many circumstances will readily divide. Referring to the use of protoplasts in genetic engineering of cereals, a leading researcher in corn transformation stated:

Although transgenic cereals can be regenerated from protoplasts in rice, and one has reason to hope that this will also be possible from other cereals, it would be unfortunate if gene technology with cereals has to rely on this [the use of protoplasts] tedious, unpredictable, and unreliable method.

I. Potrykus, *Biotechnology*, 535 (June, 1990).

To date, there is only one report of fertile transgenic plants arising from transformed maize protoplasts. G. Donn et al., *Abstracts VIIth International Congress on Plant Tissue and Cell Cult.*, Amsterdam A2-38 (Jun. 24-29, 1990). The transformation was by polyethylene glycol (PEG) mediated DNA uptake by the protoplasts not via electroporation. While a number of reports have disclosed the introduction of foreign DNA into *Zea mays* protoplasts or basal leaf segments cells or tissue by electroporation, these reports have involved either the transient transformation of the target material, or the stable transformation of tissue which is non-regenerable or was found to be nonfertile.

The difficulties associated with maintaining viability and regeneration capacity of electroporated plant protoplasts may be circumvented by the electroporation of DNA into cells which maintain a major portion of the cell wall. Attempts to do this have been unsuccessful, with one exception. J. S. Lee et al., *Korean J. Genetics*, 11, 65 (1989) reported successful stable transformation of tobacco (a dicot) cells. These cells were not enzyme-treated prior to electroporation. Other reports have disclosed only transient expression of the introduced DNA.

Marikawa et al., *Gene*, 41, 121 (1986) prepared cell suspensions directly from tobacco leaves using macerozyme. The cell suspensions were shown to be transiently transformable via electroporation, although fertility and regenerability were not determined. The treatment of cells with pectinolytic enzymes prior to electroporation in a dicot was reported to yield the transient transformation of sugar beet suspension tissue by Lindsey et al., *Plant Molec. Biol*, 10, 43 (1987). However, in sugar beets the use of pectinase- or pectolyase-treated cells afforded significantly lower levels of transient transformation than did the use of protoplasts. Subsequent sugar beet transformation studies by this group returned to the use of protoplasts. Lindsey et al., *Plant Cell Reports*, 8, 71 (1989).

Electroporation represents one of the few, if not only, methods for high frequency plant transformation. Therefore, a need exists for a method to adapt this technology to transform cereals, particularly maize, with heterologous DNA, so that the DNA is stably integrated in the plant genome and inherited by progeny of the transformed plants.

SUMMARY OF THE INVENTION

The present invention provides a method for the transformation of the cells of monocots such as *Zea mays* at unexpectedly high frequency, by electroporation. The invention also provides fertile monocots such as transgenic corn plants, which can be prepared from the transformed cells of the invention. The invention provides a method for increasing the susceptibility of monocot cells to the introduction of recombinant DNA (which has also been referred to in the art as "heterologous," "foreign" or "exogenous" DNA), while substantially preserving the viability and regenerative capacity of the cells. As used herein, regenerative capacity refers not only to the ability of a cell to regenerate into a plant, but also that the regenerated plant be fertile and to pass on the recombinant DNA to its progeny.

The present invention obviates the need to use protoplasts in the transformation of monocots by electroporation. The invention employs certain cell wall-degrading polysaccharidase enzymes to render target monocot cells, such as *Zea mays* cells substantially more susceptible to transformation by electroporation than untreated cells. Target cells are transformed in accord with the invention at high frequency and have substantially improved viability and regenerative capacity, as compared to protoplasts from the same tissue. Once transformed with recombinant DNA, a substantial number of a population of the cells can be used to regenerate a population of fertile transgenic plants.

In the context of the invention, the term "high transformation frequency" is defined to mean above 2000 transformed sectors per 0.1 ml packed cell volume, wherein the term "sector" is as defined hereinbelow.

BRIEF DESCRIPTION OF THE DRAWINGS

FIGS. 2A and 2B depicts a schematic map of 6.1 kb plasmid pBII221(FIG. 1A) and a partial restriction endonuclease map of the chimeric beta-glucuronidase gene (GUS) is shown in FIG. 1B.

DESCRIPTION OF THE PREFERRED EMBODIMENTS

Figure 1A:
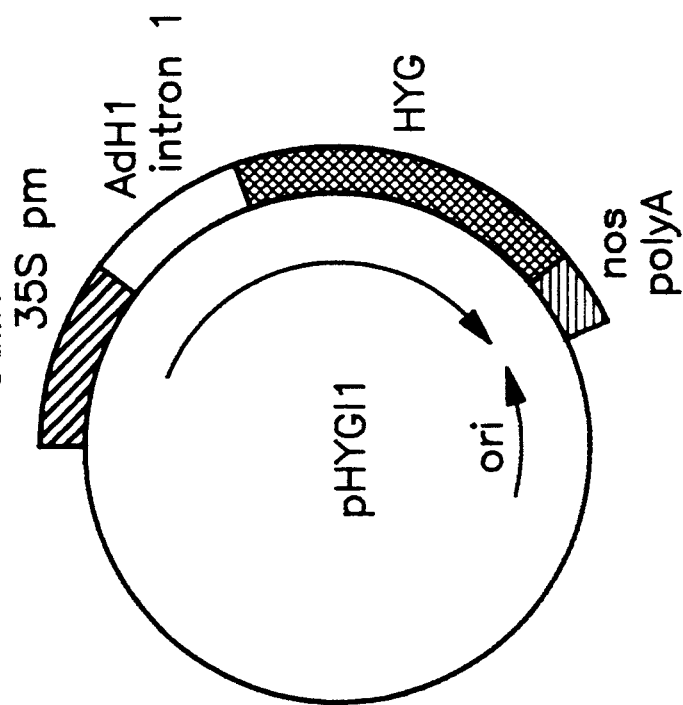
FIGS. 1A and 1B depicts a schematic map of 5.8 kb plasmid pPolHYGI-3 (FIG. 1A) and a partial restriction endonuclease map of the chimeric hygromycin B phosphotransferase gene (HPT) is shown in FIG. 1B.

The present invention is directed to a method for the production of fertile transgenic Zea mays plants and to plant parts such as cells, plant tissues, and seeds derived from such transgenic plants, as well as the subsequent progeny and the products derived therefrom. The transgenic plants produced herein include all plants of the Zea mays species, including field corn, popcorn, sweet corn, flint corn and dent corn.

"Transgenic" is used herein to include any cell, cell line, callus, tissue, plant part or plant which contains recombinant DNA that was introduced into plant material by a process of genetic engineering, as opposed to a process occurring in nature, or which was initially introduced into a plant species by a genetic engineering process and was subsequently transferred to later generations by sexual or asexual cell crosses or cell divisions.

By "heritable" is meant that the DNA is capable of transmission through a complete sexual cycle of a plant, i.e. passed from one plant through its gametes to its progeny plants in the same manner as occurs in normal corn. "Heritable" as used herein includes maternal or paternal inheritance, in addition to standard Mendelian inheritance.

The transgenic plants of this invention may be produced by (i) making suspension cultures of Zea mays cells from embryogenic callus, (ii) partially enzymatically degrading the cell walls of said cells by the controlled exposure of said cells to certain pectin-degrading enzymes to yield novel cells termed "transformation-competent cells." Transformation-competent cells are defined to mean cells with increased capacity for DNA uptake, expression and integration via electroporation, (iii) transforming said transformation-competent cells with recombinant DNA by electroporation, (iv) optionally identifying or selecting transformed cells, and (v) regenerating fertile transgenic plants from the transformed cells. Some of the plants of this invention may be produced from the transgenic seed produced by the fertile transgenic plants, or conventional crossbreeding techniques can be used to develop commercial hybrid seed from said transgenic plants, containing the recombinant DNA.

Therefore, in a preferred embodiment, the present invention provides a method for producing a population of Zea mays cells, a substantial number of which are susceptible to stable transformation, comprising the steps of:

(a) generating a culture of embryogenic Zea mays callus tissue on a solid tissue culture medium;

(b) transferring said cultured callus tissue to liquid growth media to yield a suspension cell culture of Zea mays cells; and (c) incubating a population of the cultured Zea mays cells with at least one pectin-degrading enzyme in an aqueous osmoticum to yield a population of viable Zea mays cells, wherein a substantial number of said cells can be stably transformed with recombinant DNA by electroporation to yield a population of transgenic Zea mays cells, and wherein a substantial number of said transgenic cells can be regenerated into a population of fertile, transgenic Zea mays plants containing said recombinant DNA which is heritable.

Preferably, the cultured Zea mays callus tissue is generated from immature maize embryos, and is of "friable consistency," (also referred to as type II callus) as that term is employed and defined hereinbelow. Also, prior to step (c), it is preferred to declump, or to further disperse the cultured Zea mays cells, to increase the cell wall surface area available to enzymatic action, e.g., by forcing the cultured cells through a sieve or filter.

Furthermore, as used herein with respect to the ability to transform or to regenerate cells of a Zea mays population, the term "a substantial number" is to be understood with reference to the working examples presented hereinbelow.

The present invention also provides transgenic Zea mays callus tissue which is prepared by electroporating the enzyme-incubated callus cells in the presence of recombinant DNA in aqueous, buffered osmoticum, to yield a population of transgenic Zea mays cells that have been stably transformed with said DNA; and regenerating callus tissue from said transgenic cells, so that a population of transgenic Zea mays plants comprising said DNA which is heritable, can be regenerated from said callus tissue.

The present invention also provides transgenic Zea mays plants produced by regenerating plants from this transgenic callus tissue.

As used herein, the term "osmoticum" refers to one or more compounds that may be added to the extracellular medium which are capable of maintaining an osmotic balance between the extracellular medium and the interior of the transformation-competent Zea mays cells, so that cell viability is maintained. Preferred osmotica are sugars such as fructose, sucrose and the like, and polyols, preferably ($C_2$–$C_6$) polyols such as glycerol, sorbitol and mannitol.

I. Plant lines and tissue cultures

A. Cells

The Zea mays cells which have been found useful as starting materials in the present transformation method are those callus cells which are regenerable, both before and after undergoing suspension culturing and the selection regimens detailed further below. Generally, these cells will be derived from meristematic tissue which contain cells which have not yet terminally differentiated. In maize, such tissue comprises tissues found in juvenile leaf basal regions, immature tassels, immature embryos, mature embryos, and coleoptilar nodes. Preferably, immature embryos are used.

B. Suspension Cell Cultures

Methods of preparing and maintaining callus from such maize tissue are well known in the art and details on so doing are available in the literature, c.f. R. Phillips et al., *Corn and Corn Improvement*, Agronomy Society of America (3d ed., 1988) at pages 345–387.

While regenerable maize suspension cell cultures can be initiated from a number of plant tissues, the cell cultures useful herein are preferably derived from callus that is generated from immature maize embryos which are removed from the kernels of an ear when the embryos are about 1–3 mm in length. This length generally is attained about 9–14 days after pollination. Under aseptic conditions, the embryos are placed on conventional solid media with the embryo axis down (scutellum up). Callus tissue appears from the scutellum after several days to a few weeks. After the callus has grown sufficiently, the cell proliferations from the scutellum may be evaluated for friable consistency and the presence of well-defined embryos. By "friable consistency" is meant that the tissue is easily dispersed without causing injury to the cells. Tissue with this morphology is then transferred to fresh media and subcultured on a routine basis about every two weeks.

The callus initiation media is preferably solid because callus cannot be readily initiated in liquid medium. The initiation/maintenance media (F media) is typically based on the N6 salts of C. C. Chu et al., *Sci. Sin. (Peking)*, 18, 659 (1975) as described in C. L. Armstrong et al., *Planta*, 164, 207 (1985) or the MS salts of T. Murashige et al., *Physiol. Plant*, 15, 473 (1962). The basal medium is supplemented with sucrose and generally with an auxin such as 2,4-dichlorophenoxyacetic acid (2,4-D) or dicamba. Supplements such as L-proline and casein hydrolysate have been found to improve the frequency of initiation of callus cultures, morphology, and growth. The cultures are generally maintained in the dark, though low light levels may also be used. The level of synthetic hormone 2,4-D, necessary for maintenance and propagation, should be generally about 0.3 to 3.0 mg/l. The precise methodology for the production of suspension cultures is not critical to the invention. Friable embryogenic callus which is more than about 3 months and up to about 36 months of age has been found to give rise to suspension cell cultures with a sufficiently high level of regenerability and thus is currently preferred.

Once established, e.g., after 4–6 months, the type II callus is transferred to liquid growth media. Methods and references for the production of regenerable suspension cell cultures are given by C. E. Green et al. in *Maize for Biological Research*, Plant Molec. Biol. Assoc. (1982) at pages 367–372, R. Phillips et al., *Corn and Corn Improvement*, Agronomy Soc. Amer., (3d ed., 1988) at pages 345–387, and I. Vasil, *Cell Culture and Somatic Cell Genetics of Plants*, Vol. I, *Laboratory Procedures and Their Applications*, Academic Press (1984) at pages 152–158. Typically, the liquid growth media for suspension cultures is of similar formulation to the solid callus induction media. ABA (abscisic acid) ($10^{-7}$M) may be added to the liquid growth media to augment regenerative capacity and enhance culture vitality. It is preferred that the callus not be sieved prior to introduction into the liquid media.

The cultures in liquid media are subcultured as appropriate for maintaining active growth and their regenerative properties. In preferred embodiments, the cultures are subcultured once a week at a 1:8–9 dilution with fresh growth medium.

The regenerative capacity of a particular suspension cell culture may be readily determined by transferring samples thereof to callus maintenance medium, allowing callus growth and monitoring the formation of shoots, roots, and plantlets following subsequent culturing onto regeneration medium (e.g., having increased sucrose and decreased 2,4-D). The relative number of plantlets arising per Petri dish or per gram fresh weight of callus tissue may be used as a rough quantitative estimate of regeneration capacity. Generally, a culture will produce at least one plant per 1–6 gms, preferably per 1–2 gms of callus tissue.

II. DNA Used for Transformation

As used herein, the term "recombinant DNA" refers to a DNA segment that has been derived or isolated from any source, that may be subsequently chemically altered and later introduced into *Zea mays*. An example of such DNA could include a DNA sequence that is identified as a useful fragment within a given organism, and which is then chemically synthesized in essentially pure form. An example of recombinant DNA "isolated" from any source would be a useful DNA sequence that is excised or removed from said source by chemical means, e.g., by the use of restriction endonucleases, so that it can be further manipulated, e.g., amplified, for use in the invention.

Therefore "recombinant DNA" includes completely synthetic DNA, semi-synthetic DNA, DNA isolated from biological sources, and DNA derived from introduced RNA. Generally, this DNA is not originally resident in the *Zea mays* genotype which is the recipient of the DNA, but it is within the scope of the invention to isolate a gene from a given *Zea mays* genotype, and to subsequently introduce multiple copies of the gene into the same genotype, e.g., to increase the level of a given gene product.

The DNA includes but is not limited to, DNA from plant genes and non-plant genes such as those from bacteria, yeasts, animals or viruses; modified genes, portions of genes, chimeric genes, including genes from the same or different *Zea mays* genotype.

The recombinant DNA used for transformation herein may be circular or linear, double-stranded or single-stranded. Generally, the DNA is in the form of a recombinant plasmid and contains coding regions of beneficial heterologous DNA with flanking regulatory sequences which promote the expression of the DNA in the genome of the transformed corn plant. For example, the recombinant DNA may itself comprise or consist of a promoter that is active in *Zea mays*, or may utilize a promoter already present in the *Zea mays* genotype that is the transformation target.

The compositions of, and methods for, constructing DNA which can transform certain plants are well known to those skilled in the art, and the same compositions and methods of construction may be utilized to produce the recombinant DNA useful herein. The specific composition of the DNA is not central to the present invention and the invention is not dependent upon the composition of the specific transforming DNA used. K. Weising et al., *Ann. Rev. Genetics*, 22, 421

(1988) describes suitable DNA components, selectable marker genes, reporter genes, enhancers, introns, and the like, as well as provides suitable references for compositions therefrom. J. Sambrook et al., *Molecular Cloning: A Laboratory Manual*, Cold Spring Harbor Laboratory Press (2d ed., 1989), provides suitable methods of construction. Generally, the recombinant DNA will be relatively small, i.e., less than about 30 kb to minimize any susceptibility to physical, chemical, or enzymatic degradation which is known to increase as the size of the DNA increases.

Suitable recombinant DNA for use herein includes all DNA which provides for, or enhances, a beneficial feature of the resultant transgenic corn plant. The DNA may encode proteins or antisense RNA transcripts in order to promote increased food or feed values, herbicide resistance, higher yields, pest resistance, disease resistance, and the like. For example, the DNA can encode a non-regulated DHDP synthase gene such as the dap A gene for increased lysine production; *Bacillus thuringiensis* (Bt), δ-endotoxin or a protease inhibitor for insect resistance; bacterial EPSP synthase for resistance to glyphosate herbicide; and chitinase or glucan endo-1,3-β-glucosidase for fungicidal properties. The DNA can encode a seed storage protein, such as a zein protein, e.g., the 10 kd zein protein, the expression of which can lead to increased whole kernel methionine levels, or any storage protein wherein increased methionine, lysine and threonine are of particular utility.

Aside from DNA sequences that serve as transcription units or portions thereof, useful DNA may be untranscribed, serving a regulatory or a structural function. Also, the DNA may be introduced to act as a genetic tool to generate mutants and/or assist in the identification, genetic tagging, or isolation of segments of corn DNA. Additional examples may be found in Weising, cited supra.

The recombinant DNA to be introduced into the plant further will generally contain either a selectable marker or a reporter gene or both to facilitate identification and selection of transformed cells. Alternatively, the selectable marker may be carried on a separate piece of DNA and used in a co-transformation procedure. Both selectable markers and reporter genes may be flanked with appropriate regulatory sequences to enable expression in plants. Useful selectable markers are well known in the art and include, for example, antibiotic and herbicide resistance genes.

Specific examples of such genes are disclosed in Weising et al., cited supra. A preferred selectable marker gene is the hygromycin B phosphotransferase (HPT) coding sequence, which may be derived from *E. coli* and which confers resistance to the antibiotic hygromycin B. Other selectable markers include the aminoglycoside phosphotransferase gene of transposon Tn5 (AphII) which encodes resistance to the antibiotics kanamycin, neomycin and G418, as well as those genes which code for resistance or tolerance to glyphosate, 2,2-dichloropropionic acid, methotrexate, imidazolinones, sulfonylureas, bromoxynil, phosphinothricin and the like. Those selectable marker genes which confer resistance or tolerance to phytotoxins are also of commercial utility in the resulting transformed plants. Representative genes of this type are listed in Table 1, below.

TABLE 1

| Selectable Marker Genes | | |
|---|---|---|
| Resistance Gene or Enzyme | Confers Resistance to: | Reference |
| Neomycin phosphotransferase (neo) | G-418, neomycin, kanamycin | P.J. Southern et al., J. Mol. Appl. Gen., 1, 327 (1982) |
| Hygromycin phosphotranferase (hpt or hg y) | Hygromycin B | Y. Shimizu et al., Mol. Cell Biol., 6, 1074 (1986) |
| Dihydrofolate reductase (dhfr) | Methotrexate | W.W. Kwok et al., PNAS USA, 4552 (1986) |
| Phosphinothricin acetyltransferase (bar) | Phosphinothricin | M. DeBlock et al., EMBO J., 6, 2513 (1987) |
| 2,2-Dichloropropionic acid dehalogenase | 2,2-Dichloropropionic acid (Dalapon) | V. Buchanan-Wollaston et al., J. Cell. Biochem., Supp. 13D, 330 (1989) |
| Acetohydroxyacid synthase | Sulfonylurea, imidazolinone and triazolopyrimidine herbicides | P.C. Anderson et al. (U.S. Pat. No. 4,761,373); G.W. Haughn et al., Mol. Gen. Genet., 211, 266 (1988) |
| 5-Enolpyruvyl-shikimate-phosphate synthase (aroA) | Glyphosate | L. Comai et al., Nature, 317, 741 (1985) |
| Haloarylnitrilase | Bromoxynil | D.M. Stalker et al., published PCT appln. WO87/04181 |
| Acetyl-coenzyme A carboxylase | Sethoxydim, haloxyfop | W.B. Parker et al., Plant Physiol., 92, 1220 (1990) |
| Dihydropteroate synthase (sul I) | Sulfonamide herbicides | F. Guerineau et al., Plant Molec. Biol., 15, 127 (1990) |
| 32 kD photosystem II polypeptide (psbA) | Triazine herbicides | J. Hirschberg et al., Science, 222, 1346 (1983) |
| Anthranilate synthase | 5-Methyltryptophan | K. Hibberd et al., (U.S. Pat. No. 4,581,847) |
| Dihydrodipicolinic acid synthase (dap A) | Aminoethyl cysteine | K. Glassman et al., published PCT application No. WO89/11789 |

Reporter genes can be used to determine whether a given sequence of recombinant DNA can be used to transform a maize cell. Reporter genes which encode for easily assayable marker proteins are well known in the art. In general, a reporter gene is a gene which is not present in or expressed by the recipient organism or tissue and which encodes a protein whose expression is manifested by some easily detectable property, e.g., phenotypic change or enzymatic activity. Examples of such genes are provided in Weising et al., supra. Preferred genes include the chloramphenicol acetyl transferase gene (cat) from Tn9 of *E. coli*, the beta-glucuronidase gene of the uidA locus of *E. coli*, and the luciferase genes from firefly *Photinus pyramis*. An assay for expression of the reporter gene is done at a suitable time after the DNA has been introduced into the recipient cells. A preferred such assay entails the use of the *E. coli* beta-glucuronidase (GUS) gene (R. Jefferson et al., *EMBO J.*, 16, 3901 (1987)). Maize cells transformed and expressing this gene will stain blue upon exposure to substrate 5-bromo-4-chloro-3-indolyl-beta-D-glucuronide (X-GLUC), in the extra-cellular medium.

The regulatory sequences useful herein include any constitutive, inducible, tissue or organ specific, or developmental stage specific promoter which can be expressed in the particular plant cell. Suitable such promoters are disclosed in Weising et al., supra. The following is a partial representative list of promoters suitable for use herein: regulatory sequences from the T-DNA of *Agrobacterium tumefaciens*, including mannopine synthase, nopaline synthase, and octopine synthase; alcohol dehydrogenase promoter from corn; light inducible promoters such as ribulose-bisphosphate-carboxylase/oxygenase small subunit gene from a variety of species; and the major chlorophyll a/b binding protein gene promoters; 35S and 19S promoters of cauliflower mosaic virus (CaMV); developmentally regulated promoters such as the waxy, zein, or bronze promoters from maize; as well as synthetic or other natural promoters which are either inducible or constitutive, including those promoters exhibiting organ-specific expression or expression at specific development stage(s) of the plant.

Other elements such as introns, enhancers, polyadenylation sequences and the like, may also be present on the DNA. Such elements may or may not be necessary for the function of the DNA, although they can provide a better expression or functioning of the DNA by affecting transcription, stability of the mRNA, or the like. Such elements may be included in the DNA as desired to obtain the optimal performance of the transforming DNA in the plant. For example, the maize AdhIS first intron may be placed between the promoter and the coding sequence in a particular recombinant DNA construction. This intron, when included in a DNA construction, is known to generally increase expression of a gene in maize cells. (J. Callis et al., *Genes and Develop.*, 1, 1183 (1987)). However, sufficient expression for a selectable marker to perform satisfactorily can often be obtained without an intron. (T. Klein et al., *Plant Physiol.*, 91, 440 (1989)). An example of an alternative suitable intron is the shrunken-1 first intron of *Zea mays*. These other elements must be compatible with the remainder of the DNA constructions.

III. Transformation-Competent Cell Preparation and Electroporation of Suspension Cultures In order to successfully produce fertile transgenic plants by electroporation, four requirements must be met: (i) The target cells are viable; (ii) The target cells are able to take up the recombinant DNA at high enough frequencies to insure the stable transformation of a useful number of cells; (iii) Once transformed, the recipient cells must be able to maintain cell division and regenerative capacity throughout the selection processes necessary to confirm and identify stably transformed cells; (iv) The transformed regenerated plants must transmit the "transformed condition", e.g., the introduced DNA is transmitted to progeny in functional or unaltered form, including the ability to be expressed.

An aspect of the invention is that DNA uptake during electroporation is improved through the formation of a class of altered cells which may be termed transformation-competent cells. It is believed that transformation-competent cells result from the hydrolysis of certain cell wall components, such as pectin, which may lead to enhanced permeability of the cell wall to exogenous DNA while not destroying cell viability. This is in contrast to the preparation of protoplasts in which the entire cell wall is removed by enzymatic digestion. Obvious differences between the protoplasts and the transformation-competent cells of this invention include the following. Transformation-competent cells are morphologically and physiologically distinct from protoplasts and are readily distinguishable from protoplasts. Transformation-competent cells retain the out-of-round shape of callus cells compared to protoplasts which are spherical. Transformation-competent cells, like callus cells, consist of stable cell clumps while protoplasts do not, unless they reversibly agglutinate. Tinapol BPOT, a cellulose-specific stain, stains transformation-competent cells while no staining is observed with protoplasts. Furthermore, the low solution osmolarities used during the incubation period associated with the electroporation procedure with *Zea mays* would be expected to cause the lysis of protoplasts.

In the present method the maize cells are treated to digest a portion of the cell wall with polysaccharidase enzymes such as one or more pectin-degrading enzymes. As used herein, the term "pectin-degrading enzyme" encompasses both enzymes that directly catalyze the degradation of pectin, and enzymes that catalyze the breakdown of pectin subunits. Therefore both endopectin lyase, pectin lyase, pectolyase, endopolygalacturonase, and polygalacturonase are pectin-degrading enzymes, as that term is used herein, as is pectinase itself. Other enzymes such as xylanase, cellulase, hemicellulase, driselase, transeliminase, or macerozyme, may also be useful in combination with pectin-degrading enzymes.

Monocots and dicots are significantly different with respect to pectin composition and distribution. In monocots, pectin and pectate represent only a small fraction of the cell wall constituents (1–6%). The relatively small amount of pectin is tightly bound into the cell wall. This is in contrast to dicots, where pectin is a major cell wall constituent (about 35%), and exists primarily as an homogenous layer within the cell wall. See N. Carpita, in *Physiology of Cell Expansion During Plant Growth*, D. J. Cosgrove et al., eds., Amer. Soc. Plant Physiol. (1987) at pages 28–95; and A. Darrill et al., *The Biochemistry of Plants*, 1, 91 (1980). Cereal cells in which the cell wall has been overly degraded by enzymatic treatment have poor viability and do not divide. For this reason, in the preparation of transformation-competent cells, enzymatic treatment should be carried out as long as possible, but not long enough to seriously affect either viability, mitotic activity, or regenerative capability of the suspension cultures. Preferably, about 300–5000 units of enzymatic activity, measured as maceration activity, per packed 1–2 ml of *Zea mays* cells will be introduced into the incubation medium to a total volume of about 5 ml. Maceration activity is defined here as the volume of single cells released from potato tuber slices under the conditions as specified by Ishii, *Phytopathology*, 66, 281 (1976).

In preferred embodiments of the invention, endopectin lyase (E.C. 3.2.1.15.) is used in combination with endopolygalacturonase (EC 4.2.2.3.) to generate transformation-competent cells. (Both are contained in "Pectolyase Y-23", Seishin Pharmaceutical Co., $100 \times 10^3$ maceration units/gm.) This combination of enzymes is also generically referred to as "pectolyase," and is available from Sigma Chem. Co., St. Louis, Mo.

For a dilute solution of enzyme(s) (0.1–1%), digestion time may range from about 0.75–3.0 hours, preferably from about 1.5–2.0 hours for a packed volume of about 1–2 ml of maize cells/5 ml enzyme buffer at about room temperature, preferentially at about 20°–30° C. In some embodiments of the present method, prior to treatment with enzyme(s), cells from suspension cultures are forced through a sieve, or otherwise further dispersed or declumped. Cultures prepared from clumps of cells forced through sieve size 860 μm tend to have better viability, but are transformed at lower frequency, than cultures from cells forced through 520 μm sieves. Generally, this treatment is most useful for suspension cultures containing many large clumps of cells, that is, greater in size than will pass through a 20 mesh (860 μm opening), and substantially increases the total area of cell walls which is exposed to the enzymes. Following digestion, the cells are rinsed with an amount of buffer, sufficient to substantially remove residual enzyme activity. In general, 2–3 rinses consisting of 5–15 ml of buffer per 1–2 ml of packed cells is sufficient.

The electroporation buffer formulation is also preferably optimized for cell viability and transformation. Elements of the formulation that have been optimized include the ionic composition and pH. The osmoticum species and concentration have also been optimized.

The optimal digestion conditions for any of the other enzymes, or combinations of enzymes, listed above can be determined employing another feature of the invention. To determine the appropriate digestion conditions, a transient transformation-dose response curve for various concentrations of the given enzyme may be determined. Varying amounts of digestion are performed on suspension cultures using the osmoticum conditions stipulated. The transformation-competent cells prepared thereby are then subjected to electroporation according to the conditions of the invention. A reporter gene such as the beta-glucuronidase encoding gene can be employed as the heterologous DNA. Following electroporation and recovery, cells are assayed for the expression of the reporter gene. In addition, the cells are scored for mitotic activity following the electroporation process. The appropriate concentration of enzyme will be that for which acceptable levels of mitosis ($\geq 20\%$ growth) and transient transformation (100 to >5,000 blue sectors/0.1 ml packed cells) are observed.

In addition to maintaining mitotic activity, properly prepared transformation-competent cells, unlike protoplasts, will retain the morphology of multicell clumps in culture. This is because much of the cell wall is still intact and the cells are observed to be out of round. Therefore, the remaining cell wall is stainable with cellulose stains such as Tinapol BOPT (Ciba-Geigy). This is in contrast to protoplasts which contain no stainable cell wall, since the cellulose has been completely removed.

Heterologous recombinant DNA can be introduced into the regenerable, cultures of transformation-competent cells via an electroporation process. A general description of a suitable electroporation instrument is provided in H. Potter et al., *PNAS USA*, 81, 7161 (1984). While protocols for the use of the instrument in the electroporation of maize non-regenerable protoplasts are described in M. Fromm et al., *PNAS USA*, 82, 5824 (1985), and of electroporation of maize leaf bases (R. A. Dekeyser et al., *Plant Cell*, 2, 591 (1990)), no protocols have been published for the electroporation of maize cells which can subsequently be regenerated into fertile transgenic maize plants. For electroporation of transformation-competent cells, many variations of waveform, pulse length and number can be used. Furthermore, variations in the ionic strength of the electroporation buffer may require alterations in some of these other parameters. The preferred embodiments listed below are exemplary and not meant to limit the invention.

In general, useful electroporation apparatus will consist of an electronic device containing a capacitor. The charged capacitor can then be incorporated into a circuit in series with the cells to be electroporated in an electroporation buffer. Once incorporated into the circuit, the capacitor is discharged resulting in the delivery of an exponentially decaying current pulse to the cells. Electroporation apparati are also available which deliver other waveform pulses. Protocols outlined herein may be altered to permit their use, provided acceptable levels of expression and viability are observed.

Transformation-competent cells are preferably electroporated within about 45 min. of their preparation, although longer lag periods may work. Cells left for as long as 3 hours can display acceptable transformation frequencies. The cells are electroporated in an electroporation chamber in the presence of electroporation buffer at room temperature (20°–30° C.). (See K. J. Paite, *Plant Cell Reports*, 4, 274 (1985) (chamber)). Important aspects of the electroporation buffer are the osmolarity and the ionic composition. The electroporation buffer must be compatible with, and not toxic or otherwise detrimental to the cells during its contact with them. The electroporation buffer will generally contain the recombinant DNA, a buffering agent, and an osmoticum. The buffering agent will maintain the pH of the electroporation buffer between about 7 and 7.7, preferably at about 7.5. Useable such buffers include HEPES, (N-[2-hydroxyethyl]piperazine-N'-[2-ethanesulfonic acid]) and sodium phosphate, and mixtures thereof.

The osmoticum is necessary to preserve cell viability and transformation frequency. Suitable osmotica include sugars such as inositol, fructose, and sucrose, and polyols such as mannitol, sorbitol, glycerol and the like. For all of these compounds, a concentration of approximately 0.3–0.5M was found to be optimal. The use of mannitol however, leads to consistently higher transformation frequencies than using either sorbitol or sucrose.

The recombinant DNA present in the electroporation buffer may be in supercoiled, linear single- or double-stranded form. In preferred embodiments, linear double-stranded DNA, e.g., from recombinant plasmids, is employed. Although concentrations as low as about 1 μg per 1.0 ml of electroporation buffer may be used, it is preferred that DNA be at a concentration of about 100 μg/ml or greater. These amounts represent about 1–100 μg of DNA per 0.1 ml of packed *Zea mays* cells.

IV. Selection Process

Once the transformation-competent cells have been electroporated in the presence of the recombinant DNA and the DNA has penetrated at least some of the cells, the cells are placed on a recovery medium. It is presently preferred that immediately following electroporation, cells be placed on a solid callus maintenance medium containing mannitol. After one week, the mannitol is removed. Recovery on maintenance media is continued for an additional week prior to beginning selection. The length of the recovery period may vary according to the selection agent used, and/or the number of cells electroporated. The purpose of the recovery period is to allow cells to recover from electroporation and to allow cell proliferation and stabilization in order to generate suitable numbers of cells to facilitate the selection and subsequent regeneration process. Between 1 day and 4 weeks, preferably at about 1.5–2.5 weeks, the selection regime will be initiated.

Following recovery, it is necessary to identify and select those cells which both contain the recombinant DNA and still retain sufficient regenerative capacity to form plants. There are two general approaches which have been found useful for accomplishing this. First, the transformed cells within calli or plants regenerated therefrom can be screened for the presence of the recombinant DNA by various standard methods which could include assays for the expression of reporter genes or assessment of phenotypic effects of the recombinant DNA, if any. Alternatively and preferably, when a selectable marker gene has been transmitted along with or as part of the recombinant DNA, those cells of the callus which have been transformed can be identified by the use of a selection agent to detect expression of the selectable marker gene.

Selection conditions must be chosen so as to allow growth and accumulation of the transformed cells while simultaneously inhibiting the growth of the non-transformed cells. The situation is complicated by the fact that the viability of individual cells in a population is often highly dependent on the viability of neighboring cells (K. N. Kas et al., Planta(Berl.), 126, 105 (1975)). Also, the selection conditions must not be so severe that the plant regeneration capacity of the callus cultures and the fertility of the resulting plant are destroyed. Thus, the effects of the selection agent on cell viability and morphology should be evaluated. This may be accomplished by experimentally producing a growth inhibition curve for the given selective agent and tissue being transformed beforehand. The concentration range which will inhibit growth will be established.

Selection procedures necessarily involve exposure to a toxic agent and may employ sequential changes in the concentration of the agent and multiple rounds of selection. The particular concentrations and cycle lengths will likely be varied for each agent. A currently preferred selection procedure entails growing transformed suspension cultures in the presence of hygromycin B (Calbiochem, San Diego, Calif.) at 15 mg/l for a period of 3-6 weeks followed by selection on 60 mg/l for 3-6 weeks.

Once a callus sector is identified as a putative transformant, transformation can be confirmed by phenotypic and/or genotypic analysis. If a selection agent is used, an example of phenotypic analysis is to measure the increase in fresh weight of the putative transformant as compared to a control, on various levels of the selection agent. Other analyses that may be employed will depend on the function of the recombinant DNA. For example, if an enzyme or protein is encoded by the DNA, enzymatic or immunological assays specific for the particular enzyme or protein may be used. Other gene products may be assayed by using a suitable bioassay or chemical assay. The presence of the recombinant DNA can also be confirmed by conventional procedures, i.e., by Southern blot or by polymerase chain reaction (PCR).

V. Regeneration of Plants and Production of Seed

Cell lines which have been transformed are regenerated into plants and the fertility of the resultant plants determined. Transformed cell lines which test positive by genotypic and/or phenotypic analysis are then placed on a media which promotes tissue differentiation and plant regeneration. Regeneration may be carried out in accord with standard procedures well known in the art. The procedures commonly entail reducing the level of auxin which discontinues proliferation of a callus and promotes somatic embryo development or other tissue differentiation. One example of such a regeneration procedure is described in C. E. Green et al. in *Maize for Biological Research*, Plant Molec. Biol. Assoc. (1982) at pages 367-372. The plants are grown to maturity in a growth room or greenhouse and appropriate sexual crosses and selfs are made as described by M. Neuffer, ibid. at pages 19-30.

VI. Analysis of R1 progeny

The plants regenerated from the transformed callus are referred to as the R0 generation or R0 plants. The seeds produced by various sexual crosses of the R0 generation plants are referred to as R1 progeny or the R1 generation. When R1 seeds are germinated, the resulting plants are also referred to as the R1 generation.

To confirm the successful transmission and inheritance of the recombinant DNA in the sexual crosses described above, the R1 generation is analyzed to confirm the presence of the heterologous DNA. The analysis may be performed as disclosed above for analysis of the electroporated callus for evidence of transformation, taking into account the fact that plants and plant parts are being used in place of the callus.

VII. Breeding of Genetically Engineered Commercial Hybrid Seed

Generally, the commercial value of the transformed corn produced herein will be greatest if the recombinant DNA can be incorporated into many different hybrid combinations. A farmer typically grows several varieties of hybrids based on differences in maturity, standability, and other agronomic traits. Also, the farmer must select a hybrid based upon his physical location since hybrids adapted to one part of the corn belt are generally not adapted to another part because of differences in such traits as maturity, disease, and insect resistance. As such, it is necessary to incorporate the heterologous DNA into a large number of parental lines so that many hybrid combinations can be produced containing the desirable recombinant DNA. This may conveniently be done by breeding programs in which a conversion process (backcrossing) is performed by crossing the initial transgenic fertile plant to an elite inbred line and then crossing the progeny back to the elite parent. The progeny from this cross will segregate such that some of the plants will carry the heterologous DNA whereas some will not. The plants that do carry the DNA are then crossed again to the elite parent resulting in progeny which segregate once more. This crossing is repeated until the original elite line has been converted to a genetically engineered line containing the recombinant DNA and also possessing all other important attributes originally found in the elite parent. A separate backcrossing program will be used for every elite line that is to be converted to a genetically engineered elite line. It may be necessary for both parents of a hybrid seed corn to be homozygous for the recombinant DNA. Corn breeding and the techniques and skills required to transfer genes from one line or variety to another are well-known to those skilled in the art. Thus, recombinant DNA can be introduced into lines or varieties which do not generate the appropriate calli.

VIII. Uses of Transgenic Plants

The transgenic plants produced herein are useful for a variety of commercial and research purposes. Transgenic plants can be created for use in traditional agriculture to possess traits beneficial to the grower (e.g. agronomic traits such as pest resistance or increased yield), beneficial to the consumer of the grain harvested from the plant (e.g. improved nutritive content in human food or animal feed), or beneficial to the food processor (e.g. improved processing traits). In such uses, the plants are generally grown for the use of their grain in human or animal foods. However, other parts of the plants, including stalks, husks, vegetative parts, and the like, may also have utility, including use as part of animal silage or for ornamental purposes (e.g. Indian corn). Often chemical constituents (e.g. oils or starches) of corn and other crops are extracted for food or industrial use and transgenic plants may be created which have enhanced or modified levels of such components. The plants may also be used for seed production for a variety of purposes.

Transgenic plants may also find use in the commercial manufacture of proteins or other molecules encoded by the recombinant DNA contained therein, where the molecule of interest is extracted or purified from plant parts, seeds, and the like. Cells or tissue from the plants may also be cultured, grown in vitro, or fermented to manufacture such molecules, or for other purposes (e.g. for research).

The transgenic plants may also be used in commercial breeding programs, or may be crossed or bred to plants of related crop species. Improvements encoded by the recombinant DNA may be transferred, e.g. from corn cells to cells of other species e.g. by protoplast fusion.

The transgenic plants may have many uses in research or breeding, including creation of new mutant plants through insertional mutagenesis, in order to identify beneficial mutants that might later be created by traditional mutation and selection. The methods of the invention may also be used to create plants having unique "signature sequences" or other marker sequences which can be used to identify proprietary lines or varieties.

EXAMPLES

The following non-limiting examples are illustrative of the present invention. They are presented to better explain the general procedures which can be used to prepare the fertile *Zea mays* plants of this invention which stably express the recombinant DNA and which transmit that DNA to progeny. All parts and percents are by weight unless otherwise specified. It must be recognized that a specific transformation event is a function of the amount of material subjected to the transformation procedure. Thus when individual situations arise in which the procedures described herein do not produce a transformed product, repetition of the procedures will be required for success.

Friable, embryogenic callus cultures identified hereinafter as AB lines, were initiated from hybrid immature embryos derived from hybrids produced by pollination of inbred line A188 plants (University of Minnesota, Crop Improvement Association) with pollen of elite inbred line B73 plants (Iowa State University).

EXAMPLE 1

Preparation of Plasmids: pPolHYGI-3 and pBII221

Figure 1B:

The plasmid pPolHYGI-3 was constructed in the vector pPolink2-6 by using standard recombinant DNA techniques. The vector pPolink2-6 consists of the large EcoRI-SalI fragment (3.1 Kb) of pBR328 (X. Soberon, et al., *Gene*, 9, 287 (1980)) and a 65 bp region containing multiple cloning sites. The plasmid pPolHYGI-3 contains the hygromycin β-phosphotransferase (HPT) coding sequence from *E. coli* (L. Gritz et al., *Gene*, 25, 179 (1983)) flanked at the 3'end by the nopaline synthase (nos) polyadenylation sequence of Agrobacterium tumefaciens (M. Breven et al., *Nucl. Acids Res.*, 11, 369 (1983)) and at the 5' end by a 553 bp BclII-BamHI fragment containing the maize AdhIS first intron (J.Callis et al., *Genes & Develop.*, 1, 1183 (1987)). Expression is driven by the cauliflower mosiac virus (CaMV) 35S promoter (H. Guilley et al., *Cell*, 30, 763 (1982)) located upstream from the hygromycin β-phosphotransferase coding sequence. For electroporation studies, plasmid DNA was linearized at the unique XhoI restriction site located at the 3' end of the nos polyadenylation sequence. A map of pPolHYGI-3 is provided as FIG. 1.

pBII221 contains the *E. coli* β-glucuronidase coding sequence (GUS) flanked at the 5' end by the CaMV 35S promoter and at the 3' end by the nos polyadenylation sequence. The plasmid was constructed by inserting the maize Adh1S first intron between the 35S promoter and the coding sequence of pBI221 (R. Jefferson et al., *(EMBO J.*, 16, 3901 (1987)). For electroporation studies, plasmid DNA was linearized at the unique EcoR1 restriction site located at the 3' end of the nos polyadenylation sequence. A map of pBII221 is provided as FIG. 2.

EXAMPLE 2

Regeneration of Electroporated Transformation-competent Cells Without Selection

A. Preparation of callus and suspension cell cultures

Hybrid ears were harvested when embryos had reached a length of 1.5 to 2.0 mm. The whole ear was surface sterilized in 50 v/v commercial bleach (2.63% w/v sodium hypochlorite) for 20 minutes at room temperature. The ears were then washed with sterile distilled, deionized water. Immature embryos were aseptically isolated and placed on nutrient agar initiation/maintenance media with the root/shoot axis exposed to the media. Initiation/maintenance media (F medium) consisted of N6 basal media (Chih-ching in *Proceedings of Symposium on Plant Tissue Culture*, May 25–30, 1978, Science Press, Peking, pp. 43–50) with 2% (w/v) sucrose, 1.5 mg/liter 2,4-D, 6 mM proline, 200 mg/l casein hydrolysate and 0.25% Gelrite (Kelco, Inc., San Diego). The pH was adjusted to 5.8 prior to autoclaving.

The immature embryos were incubated at 25° C. in the dark. Cell proliferation from the scutellum of the immature embryos was evaluated for friable consistency and the presence of well defined somatic embryos. Tissue with this morphology was transferred to fresh media 10 to 14 days after the initial plating of the immature embryos. The tissue was then subcultured every 14–21 days. Sixty to eighty mg quantities of tissue were removed from pieces of tissue that had reached a size of approximately one gram and transferred to fresh media. Subculturing involved careful visual monitoring to maintain friable, embryogenic tissue. The presence of somatic embryos indicated that the cultures would give rise to plants under the proper conditions.

Liquid suspension cell cultures were initiated from established plated callus cultures. The liquid medium consisted of F medium inoculated with $10^{-7}$ MABA after autoclaving. Suspension cultures were subcultured weekly by diluting the original volume 1:9 with fresh medium. Cultures were grown in the dark at 26° C. in 60 ml media/250 ml flask on a rotary shaker set at 150 RPM.

B. Enzymatic Pretreatment (Transformation-Competent Cell Preparation)

The AB12 suspension maize cell culture, 5 days post-subculture, was forcibly sieved through an 860 μm screen and 1.5 ml (packed volume) of the sieved suspension cells were incubated in 5 ml of a solution containing 0.5% Pectolyase Y-23 (Seishin Pharmaceutical, Tokyo, Japan), 0.2M mannitol, 0.2% BSA, 80 mM CaCl$_2$, and 20 mM MES at pH 5.8, for 60, 90, or 120 minutes. Following enzyme treatment the cells were washed as in Example 3, infra, to remove the enzyme. One half of the tissue obtained at each time point was electroporated without DNA. A 140 μF capacitor charged to 120 V was used.

After diluting 1:9 with 0.3M mannitol-containing F medium, the tissue (both electroporated and the enzyme digested-only tissue) was plated on gelrite solidified F medium plates with 0.3M mannitol for two weeks. The tissue was transferred to another round of F medium for 3 weeks.

The viability of enzyme-digested non-electroporated tissue was 50-75%. The viability of enzyme-digested electroporated tissue was 15-45%.

After three weeks on F medium the tissue was transferred to embryo and shoot development media (RM5) consisting of MS basal salts (T. Murashige et al., *Physiol. Plant*, 15, 473 (1962)) supplemented with thiamine HCl 0.5/mg/liter; 2,4-D, 0.75 mg/l, sucrose 50 g/l; asparagine 150 mg/l and gelrite 2.5 g/l. After 2.5 weeks on RM5 the differentiating, maturing tissue was transferred to R5 medium which consists of RM5 medium without 2,4-D. The cultures were kept in the dark for 10 days before being transferred to a light regime of 14 hours light and 10 hours dark at 26° C. (300 foot candles soft white fluorescent).

Plantlets, 1-3 cm high, were transferred to flow boxes containing R5 media (Plantoon, Flow Laboratories, McLean, Va.) for further development. When plants reached the two to three leaf stage they were transferred to vermiculite for 1-2 weeks, exposed to light at 2600 foot candles, and watered weekly with a weak Peters fertilizer. The plants were transferred to soil and grown to maturity.

The regenerated corn plants (approximately 10/treatment) were selfed or outcrossed. No differences in morphology, phenotype, or fertility were seen in the regenerated plants from enzyme-treated electroporated suspension cells compared to those from enzyme-treated, non-electroporated suspension cells compared to those from non-enzyme treated, non-electroporated suspension cells. Greater than 97% of the plants were fertile. Seed set averaged 30 seeds/ear.

EXAMPLE 3

Preparation of Transgenic Zea Mays Corn Cells from Transformation-Competent Cells A. Pretreatment of Cells Suspension cell cultures from the AB12 line were prepared as described in Example 2. Suspension cells, 3-7 days post subculture, were force-sieved through an 860 μm screen, and 1.0 ml (packed volume) of sieved suspension cells were incubated in 3 ml of 0.5% Pectolyase Y-23, 0.2M mannitol, 0.2% bovine serum albumin (BSA), 80 mM calcium chloride (CaCl$_2$) and 20 mM 2-(N-morpholino)-ethane sulfonic acid (MES) at pH 5.6, to form transformation-competent cells. The incubation was carried out for 90 minutes at 26° C. on a tabletop shaker (40-60 RPM) in the dark. The transformation-competent cells were washed two times with 10 ml of 0.2M mannitol, 80 mM calcium chloride, 0.1% BSA, and 20 mM MES at pH 5.6 followed by two 10 ml rinses of electroporation buffer consisting of 10 mM HEPES and 0.4M mannitol. The pH was adjusted to 7.5.

B. Electroporation

All steps in the electroporation procedure were performed at room temperature. One hundred μg of pPol-HYGI-3 linearized DNA was incubated in 0.5 ml of electroporation buffer for five minutes at room temperature. To this solution, 0.2 ml packed volume of enzyme-treated suspension cells, suspended in 0.5 ml of electroporation buffer, were added.

One half ml aliquots of cells and DNA in electroporation buffer were transferred to the electroporation chamber which was placed in a sterile 60×15 mm Petri plate. An electrical pulse was passed through the cells from a 140 μF or a 250 μF capacitor which was charged to 70 V with an ISCO model 494 power supply (280 V/cm field strength, 40-80 ms pulse decay time; exponential pulse).

Approximately ten minutes post-electroporation, the cells were diluted 1:10 with F medium containing 0.3M mannitol. Cells were centrifuged and were plated on gelrite solidified F medium containing 0.3M mannitol overlaid with two layers of Whatman #1 4.25 cm filter discs. Excess liquid was removed. Plates were kept in the dark at 26° C. After 7 to 10 days, the cells and filter paper were transferred for one week to F medium plates before being transferred to selection media. Viability of cells after electroporation was 15-35%.

C. Hygromycin Selection

Approximately two weeks after electroporation, all tissue was transferred to plates of F medium containing 15 mg/l Hygromycin B (Calbiochem) added to autoclaved media cooled to 45° C.

(i) Line 43: A sector of tissue designated transformed line 43, resulted from electroporation using a 250 μF capacitor charged to 70 V. These cells remained on the hygromycin (15 mg/l) plates for 6 weeks. Line 43 grew well while most of the remaining tissue grew poorly. This sector was transferred to F medium plates containing 60 mg/l hygromycin B. After 3 weeks, the tissue was growing vigorously and transferred to a second round of selection on 60 mg/l hygromycin. All control tissue was dead after 2 rounds on the 60 mg/l hygromycin plates. Line 43 was kept on these plates and also transferred to F medium. After 5 days some tissue from F medium was frozen for DNA extraction.

(ii) Line 18: A sector of tissue designated transformed line 18 resulted from electroporation via discharging a 140 μF capacitor charged to 70 V. This line was subjected to the same selection protocol as line 43, except it was exposed to 2 passages on plates containing hygromycin (15 mg/l) for 3 weeks each. The same results were observed as in the case of line 43.

Line 43 was transferred to RM5 and is presently on R5. Line 18 was transferred to RM5, R5 and was then planted in soil. The plantlets look healthy and have normal morphology.

D. Confirmation of Transformation of Callus

To show that callus lines 18 and 43 had acquired the hygromycin resistance gene, Southern blots of lines 18 and 43 were prepared as follows. DNA was isolated from the above callus lines and from unselected control callus by freezing 1–6 g of callus in liquid nitrogen and grinding it to a fine powder which was then transferred to a 50 ml centrifuge tube containing 12.5 ml of extraction buffer (7M urea, 250 mM NaCl, 50 mM Tris-HCl pH 8.0, 20 mM EDTA pH 8.0, 1% sarcosine). To this mixture was added 12.5 ml of phenol:chloroform:isoamyl alcohol (25:25:1) equilibrated with 0.1M Tris-HCl, pH 8.0. The tubes were then vigorously shaken for 5 min and incubated at 25° C. for 15 min. Samples were transferred to 30 ml Oak Ridge tubes and centrifuged at 8,000 rpm for 15 min at 4° C. The supernatants were pipetted through miracloth (Calbiochem, La Jolla, Calif.) into 50 ml centrifuge tubes and reextracted with the phenol:chloroform:isoamyl alcohol mixture. After centrifugation, the supernatants were extracted with an equal volume of chloroform:isoamyl alcohol (25:1) for 5 min. and centrifuged as above.

DNA was precipitated from the supernatants by adding 2.0 ml of 4.4M ammonium acetate, pH 5.2 and 12 ml of isopropanol and incubating on ice for 15 min. DNA was pelleted by centrifuging at 8,000 rpm for 5 min at 4° C. The DNA pellets were successively washed with 70% ethanol and 100% ethanol and dried prior to dissolving in TE-1 buffer (10 mM Tris-HCl pH 8.0, 1 mM EDTA). DNA was further purified by either treatment with pancreatic RNase and proteinase K or by CsCl-ethidium bromide gradient centrifugation. Pancreatic RNase A (Sigma Chemical Company) which was heated at 100° C. for 15 min prior to use, was added to the DNA samples to a concentration of 100 µg/ml. After a 1 hr incubation at 37° C., sodium dodecyl sulfate (SDS) was added to 0.5% and proteinase K (Boehringer Mannheim, Indianapolis, Ind.) to 25 µg/ml. DNA samples were incubated for an additional 1 hr at 37° C. and then were successively extracted with phenol:chloroform:isoamyl alcohol and chloroform:isoamyl alcohol as above. DNA was precipitated by adding 1/10 volume of 3M sodium acetate and 2 volumes of ethanol and incubating at −20° C. for 20 min. DNA was pelleted by centrifugation, washed successively with 70% and 100% ethanol, dried and resuspended in TE-1 buffer.

The isolated DNA (10–30 µg) was digested with either BamHI or HindIII (New England Biolabs, Beverly, Mass.) following the conditions specified by the supplier and subsequently electrophoresed in a 0.8% w/v agarose gel (Seakem GTG agarose, FMC Corporation, Pine Brook, N.J.) at 20 V for 16 hr in TAE buffer (40 mM Tris-acetate pH 8.0, 2 mM EDTA). The DNA within the gel was depurinated by soaking the gel in 0.25M HCl for 6 min and then denatured and cleaved by soaking the gel in 0.4M NaOH for about 30 min. DNA was blotted onto a Gene Screen Plus Nylon membrane (New England Nuclear, Boston, Mass.) by capillary transfer overnight in 0.4M NaOH. After washing the membrane twice in 0.2M Tris-HCl pH 7.4/0.15M NaCl for 15 min, the membrane was baked at 80° C. for 2 hrs under vacuum.

Prehybridization treatment of membranes was done in hybridization solution (0.5M sodium phosphate pH 7.2, 7% SDS, 0.05% sodium pyrophosphate, 1 mM EDTA, and 50 µg/ml denaturated salmon sperm DNA) using 0.15 ml hybridization solution per cm² of membrane. Prehybridization was carried out at 65° C. for 4 hrs.

Figure 3A:
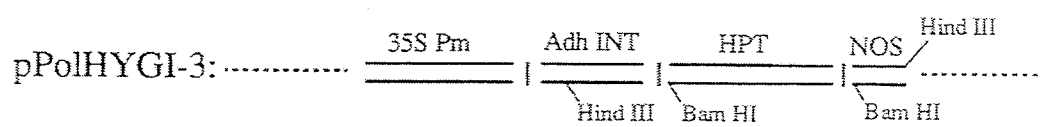
FIG. 3A is a schematic depiction of both the probe and template DNA used in the Southern blotting carried out in Example 3 and also the chimeric hygromycin B-phosphotransferase gene.
Figure 3B:
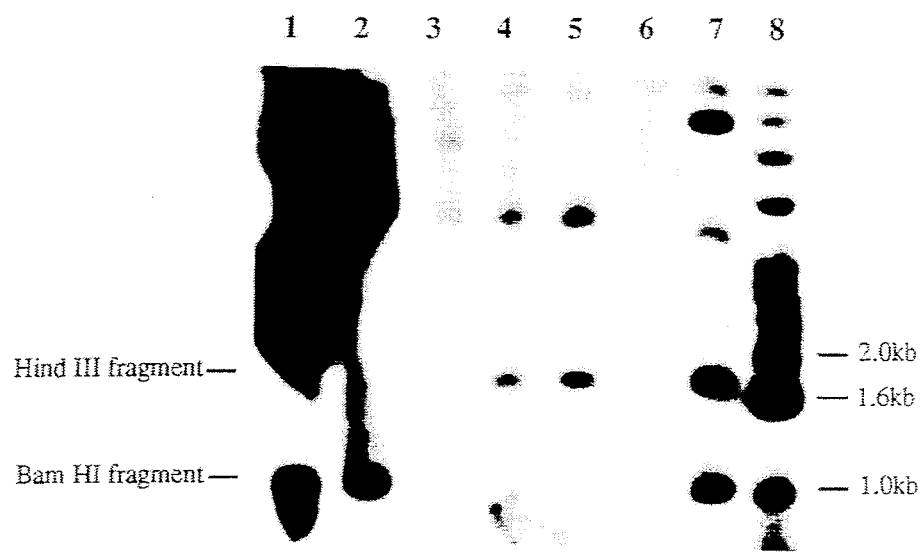
FIG. 3B is a photographic depiction of the Southern blots obtained from transformed lines 18 and 43 of Example 3.

A $^{32}$P labeled probe was prepared by random primer labeling using a Random Primed DNA Labeling Kit (Boehringer Mannheim, Indianapolis, Ind.) as per the supplier's instructions with $^{32}$P-dCTP (ICN Radiochemicals, Costa Mesa, Calif.). The template DNA used was the 1055 bp BamHI fragment of pPolHYGI-3, which is the HPT coding sequence (FIG. 3, Panel A). The fragment was gel purified.

Hybridization was performed with fresh hybridization solution containing heat-denatured probe ($10^7$ cpm/11×14 cm membrane). Incubation was at 65° C. for 18 hrs.

Membranes were washed successively with the following solutions for 30 min at 65° C.: 1XSSC (0.15M NaCl, 0.015M sodium citrate pH7.0), 1% SDS; 0.5XSSC, 1% SDS; 0.3XSSC, 1% SDS; and 0.1 X SSC, 1% SDS. Membranes were exposed at −70° C. to Kodak X-OMAT AR film with an intensifying screen.

The autoradiograph is shown in FIG. 3, Panel B. Lane 8 contains a [$^{32}$P]-radiolabeled 1 kb DNA ladder (GIBCO BRL, Gaithersberg, Md.) which served as a molecular weight standard for linear double stranded DNA. Lane 7 contains 50 pg each of pPolHYGI-3 DNA cut separately with BamHI and HindIII. BamHI restricted DNA from callus lines 18 (lane 1) and 43 (lane 2) showed an evident band that co-migrated with the BamHI fragment from pPolHYGI-3 (lane 3) which contains the entire coding sequence for the HPT gene (FIG. 3, Panel A). This band was not observed in control callus DNA cut with the same enzyme. Similarly, Hind III restricted DNA from callus lies 18 (lane 4) and 43 (lane 5) showed an evident band that co-migrated with the HindIII fragment from pPolHYGI-3 (lane 7) which contains the nucleotide sequences corresponding to part of the AdhIS intron and both the entire HPT gene and the nos poly-adenylation region (FIG. 3, Panel A). This band was not found in control callus DNA cut with HindIII (lane 6). These data demonstrate that the HPT coding sequence is present in DNA from callus lines 18 and 43.

EXAMPLE 4

Mannitol Concentration Optimization

A. Electroporation Buffers

Suspension cell line AB194qq, prepared as described in Example 2, was employed. The cells were forced through a 520 µm screen, treated with 0.5% Pectolyase Y-23 for 2 hours, mixed with electroporation buffer containing 100 µg/ml of linearized DNA from plasmid pBII221, varying concentrations of mannitol, and electroporated by discharging a 140 µF capacitor charged to 160 V as described in Example 3. Tissue was assayed for GUS activity as in Example 6. The number of blue sectors was counted after a three hour incubation. The results of this study are summarized in Table 2, below.

TABLE 2

| Conc. Mannitol | Average Number of Tissue Sectors Expressing GUS Activity |
|---|---|
| 0 | 0 |
| 0.2 M | 120 |
| 0.3 M | 1080 |
| 0.4 M | 1730 |
| 0.5 M | 1370 |

From the data given in Table 2, it can be seen that 0.4M mannitol in the electroporation buffer gave the highest level of transient expression.

A second study using 0.4–0.8M mannitol was carried out as described above, but using AB12 suspension cells, an 860 μm sieve, a 90 minute pectolyase treatment and 50 μg/ml linearized pBII221 DNA. The results indicated that transient expression fell off rapidly at mannitol concentrations above 0.4M.

EXAMPLE 5

Osmoticum Optimization

In accord with the procedures of the first study of Example 4, AB12 suspension cells were digested with Pectolyase Y-23 and electroporated (140 μF-140 V) in the presence of 50–100 μg/ml of linearized pBII221 in an electroporation buffer containing various concentrations of glycerol, sucrose, sorbitol or mannitol. Transient GUS expression was assayed as in Example 6. The results of this study, summarized in Table 3, below, indicated that mannitol was the superior osmoticum.

TABLE 3

| Study | Osmoticum | | Avg. No. of Tissue Sectors Expressing GUS Activity |
|---|---|---|---|
| Sectors | | | |
| (A) | 0.4 M | mannitol | 1875 |
| | 1.1 M | sucrose | 11 |
| | 0.2 M | sucrose | 562 |
| | 0.3 M | sucrose | 1262 |
| | 0.4 M | sucrose | 1225 |
| | 0.5 M | sucrose | 357 |
| (B) | 0.4 M | mannitol | 1440 |
| | 0.2 M | sorbitol | 25 |
| | 0.3 M | sorbitol | 265 |
| | 0.4 M | sorbitol | 470 |
| | 0.5 M | sorbitol | 250 |
| (C) | 0.4 M | mannitol | 5750 |
| | 1% | glycerol | 70 |
| | 5% | glycerol | 387 |
| | 10% | glycerol | 7 |
| | 20% | glycerol | 0 |

B. Enzyme Incubation Medium

Enzymatic digestion of suspension culture cells to prepare transformation-competent cells was performed under varying mannitol concentrations and then electroporation was performed.

Suspensions of cultured AB194qq maize cells were forced through a 520 μm screen. The sieved cells were digested with 0.5% Pectolyase Y-23. The incubation medium was modified to contain 0, 0.2M, 0.3M, or 0.4M mannitol. Cells were digested for 90 minutes. Electroporation was carried out as in example 2 with 0.3M mannitol (rather than 0.4M mannitol) in the electroporation buffer with 100 μg/ml linearized pBII221. Transient GUS expression was assayed as in Example 6.

TABLE 4

| Concentration of Mannitol in incubation buffer | Avg. No. of Tissue Sectors Expressing GUS Activity |
|---|---|
| 0 | 400 |
| 0.2 M | 12200 |
| 0.3 M | 1980 |
| 0.4 M | 1250 |

The data summarized in Table 4 indicates that 0.2 mannitol in this digestion buffer is optimal.

EXAMPLE 6

Preparation of Transformation-Competent Cells

A. Enzymatic Treatments

Suspension cell cultures of AB61 maize cells were prepared as described in Example 3, and forced through an 860 μm sieve. Enzymatic digestion of 1.5 ml of packed cells was for 90 minutes with the 5.0 ml of the indicated amount of enzyme. Subsequent electroporation with 50 μg/ml pBII221 was carried out at 140uF and 140 V. The results of staining constant weights of electroporated cells are summarized in Table 5, below. Treatment of suspension cells with 0.5% Pectolyase Y-23 gave the highest level of transient expression. No transient expression was observed in control cells not treated with enzyme.

TABLE 5

| Enzyme | Average Number of Cells Expressing GUS Activity |
|---|---|
| Expt. 1 | |
| no enzyme | 0 |
| 0.5% Pectolyase Y-23 | 802 |
| 0.5% driselase | 76 |
| 0.5% xylanase | 16 |
| Expt. 2 | |
| 0.5% Pectolyase Y-23 | 130 |
| 0.1% Pectolyase Y-23 | 14 |
| 0.03% Pectolyase Y-23 | 0 |
| 1.0% cellulase | 6 |
| 0.5% driselase | 0 |
| 0.5% Pectolyase Y-23 and driselase | 83 |
| 1% pectinase | 0 |
| Expt. 3 | |
| 0.5% Pectolyase Y-23 | 6340 |
| 1.0% driselase | 730 |
| 3% xylanase | 14 |
| 1% hemicellulase | 0 |
| 1% cellulase | 0 |
| 1% pectinase | 302 |

B. GUS Assay

After diluting 1:10 with F medium plus 0.2M mannitol, the electroporated cells were plated and the plates were sealed with parafilm and placed on a rotary shaker (40–60 RMP) in the dark at 26° C. for 16 hours. The cells were transferred to 15 ml centrifuge tubes and spun in a Beckman TJ-6 centrifuge at low speed for 5 minutes. All liquid was removed and 475 μl of GUS assay buffer was added. GUS assay buffer consisted of 1 mg/ml 5-bromo-4-chloro-3-indolyl-beta-D-glucuronide (Research Organics), 100 mM sodium phosphate (pH 7.0), 5 mM each of potassium ferricyanide and potassium ferrocyanide, 10 mM EDTA, 0.06% Triton X-100, and 0.2M mannitol. Samples were placed in a 12 well plate (Costar 3512) and incubated at 37° C. overnight. The number of blue sectors was counted in each sample. A sector is defined as one or more blue cells clustered together.

Thirty μg/ml of pBII221 were electroporated into AB61 cells which had been treated with various pairs of enzymes in accord with Part A., above. The results of the GUS assay are given in Table 6.

TABLE 6

| | Combination of Enzymes | |
|---|---|---|
| Enzymes | Relative Amounts Tissue Sectors Expressing GUS Activity | Viability |
| 0.5% Pectolyase Y-23 | ++ | 30% |
| 0.5% Pectolyase Y-23 + 0.5% driselase | ++++ | <10% |
| 0.5% Pectolyase Y-23 + 0.25% driselase | ++++ | <10% |
| 0.5% Pectolyase Y-23 | ++ | 25% |

TABLE 6-continued

| Enzymes | Combination of Enzymes Relative Amounts Tissue Sectors Expressing GUS Activity | Viability |
|---|---|---|
| 0.1% driselase | | |
| 1.0% driselase | + | 10% |
| 0.75% driselase + 0.25% Pectolyase Y-23 | + + + + | Not done |
| 0.9% driselase + 0.1% Pectolyase Y-23 | +½ | Not done |

Pectolyase and driselase in various combinations can increase transient expression greater than 2 fold compared to Pectolyase Y-23 or driselase alone; however, there is a significant loss of viability. Hemicellulase or cellulase gave no GUS expression. Transient expression was 20 fold lower using 1.0% pectinase (Worthington, Freehold, N.J.) with comparable viabilities. Pectolyase Y-23 is the preferred treatment.

EXAMPLE 7

Effect of buffer and the Concentration of KCl on Transient Transformation

Part A.

A suspension cell culture of AB194qq was forced through a 520 μm sieve and treated with 0.5% Pectolyase Y-23 for 2 hours at 26° C. The washed tissue was resuspended in electroporation solution (pH 7.5) that contained the indicated components. An equal volume of electroporation buffer containing 100 μg/ml of linearized pBII221 DNA was added and 0.5 ml aliquots of the tissue-DNA mixture were then electroporated by using a 140 μF capacitor charged to 160 volts. Tissue samples were assayed for GUS activity following a 16 hour incubation at 26° C., in accord with Example 6. The results of this study are summarized in Table 7, below.

TABLE 7

| Electroporation Buffer | KCl (mM) | Mannitol (M) | Average Number of Tissue Sectors Expressing GUS Activity |
|---|---|---|---|
| 10 mM Sodium Phosphate | 50 | 0.2 | 0 |
| | 0 | 0.2 | 86 |
| 10 mM HEPES | 50 | 0.2 | 9 |
| | 0 | 0.2 | 1104 |

Part B.

A suspension cell culture, AB194qq, was forced through a 520 μm sieve and treated with 0.5% Pectolyase Y-23 for 2 hours at 26° C. The washed tissues were resuspended in electroporation buffer that contained 10 mM HEPES (pH 7.5), 0.4M mannitol, and varying amounts of KCl. An equal volume of electroporation buffer containing 100 μg/ml of linearized pBII221 DNA was added and 0.5 ml aliquots of the tissue-DNA mixture were then electroporated by using a 140 μf capacitor charged to 160 volts. Tissue samples were assayed for GUS activity following a 16 hour incubation at 26° C., as in Part A, above. The results of this study are given in Table 8, below.

TABLE 8

| Electroporation Buffer | |
|---|---|
| KCl (mM) | Average Number of Tissue Sectors Expressing GUS Activity |
| 0 | 2940 |
| 1 | 2140 |
| 3 | 1890 |
| 10 | 350 |

These data show that transient expression is highest when the electroporation solution contains HEPES buffer and no KCl.

EXAMPLE 8

Effect of Temperature during Electroporation on the Level of Transient Transformation A suspension cell culture of AB18 maize tissue was forced through either a 520 μm or an 860 μm sieve and incubated with 0.5% Pectolyase Y-23 for 2 hours at 26° C. The washed cells were resuspended in electroporation solution (10 mM HEPES, pH 7.5, 0.4M mannitol) and placed either at 4° C. or at 25° C. (room temperature). An equal volume of electroporation solution of the same temperature containing 50 μg/ml of linearized pBII221DNA was added and then 0.5 ml aliquots of the tissue-DNA mixture were electroporated at 25° C. using a 140 μF capacitor charged to 160 volts and then immediately returned to their previous incubation temperature for 10–15 min. All tissue samples were then placed at 25° C. and diluted 10-fold with medium containing 0.3M mannitol. Tissue samples were then assayed for GUS activity following a 16 hour incubation at 26° C., as in Example 7, above. The results of this study are summarized in Table 9, below.

TABLE 9

| Sieve Size | Incubation Temperature Pre- and Post-Electroporation | Average Number of Tissue Sectors Expressing GUS Activity |
|---|---|---|
| 520μ m | 4° C. | 1190, 1115 |
| 520μ m | 25° C. | 2175, 2250 |
| 860μ m | 4° C. | 250, 360 |
| 860μ m | 25° C. | 1000, 750 |

Tissue samples that were maintained at 25° C. during the entire electroporation procedure had a 2 to 3-fold higher level of transient transformation than the corresponding samples that were incubated at 4° C. before and after electroporation. Temperature had no effect on tissue viability after electroporation.

EXAMPLE 9

Effect of Capacitance and Voltage on the Level of Transient Information

AB12 suspension cell cultures were force-sieved through a 520 μm screen and treated with 0.5% Pectolyase Y-23 for 1.5 hours at 26° C. The washed tissues were resuspended in electroporation buffer containing 10 mM HEPES (pH 7.5) and 0.4M mannitol. An equal volume of electroporation solution containing 100 μg/ml of linearized pBII221 DNA was added and 0.5 ml aliquots of the tissue-DNA mixture was electroporated using the indicated capacitors charged to varying voltages. Tissue samples were assayed for GUS activity after a 16 hour incubation at 26° C., in accord with Example 7, above. The results of a typical experiment are summarized in Table 10, below.

TABLE 10

| Capacitance (μf) | Voltage | Field Strength (Volts/cm)) | Average Number of Tissue Sectors Expressing GUS Activity | Tissue Viability |
|---|---|---|---|---|
| 250 | 140 | 560 | 6500 | + |
| 250 | 100 | 400 | 2750 | ++ |
| 250 | 70 | 280 | 200 | +++ |
| 140 | 140 | 560 | 5000 | + |
| 140 | 100 | 400 | 2485 | ++ |
| 140 | 70 | 280 | 180 | +++ |

The data on Table 10 show that when both capacitors were charged with the same voltage, slightly higher levels of transient transformation were achieved with the 250 μF capacitor. For both capacitors, transient expression increased with voltage, while cell viability decreased. The pulse decay time for the 250 μf and 140 μf capacitors was 40 and 80 msec, respectively. The 250 μF and 140 μF capacitors when charged with 70–140 V, at about 280–560 V/cm field strength, gave the best combination of transient transformation and viability compared to several other capacitors and voltages examined.

EXAMPLE 10

Effect of DNA Concentration and Form on the Level of Transient Transformation

AB18 suspension cells were sieved through a 520 μm filter and treated with 0.5% Pectolyase Y-23 for 2 hours at 26° C. The washed tissues were resuspended in electroporation buffer (10 mM HEPES, pH 7.5, 0.4M mannitol). An equal volume of electroporation solution containing either EcoR1 linearized or supercoil pBII221DNA was added at the concentrations indicated in Table 11 and 0.5 ml aliquots of the tissue-DNA mixture were electroporated using a 140 μf capacitor charged to 160 V, in accord with the procedure of Example 9. Tissue samples were assayed for GUS activity following a 16 hour incubation at 26° C., following the procedure of Example 7. The results are summarized in Table 11, below.

TABLE 11

| Amount of DNA (μg/ml) Used per Electroporation | DNA Form | Average number of Tissue Sectors Expressing GUS Activity |
|---|---|---|
| 400 | linear | 17,873 |
| 200 | linear | 15,320 |
| 100 | linear | 9,650 |
| 100 | supercoiled | 240 |
| 75 | linear | 4,940 |
| 50 | linear | 2,320 |
| 25 | linear | 1,445 |

The data on Table 11 show an approximate linear increase in transient expression with increasing amounts of linearized DNA up to 200 μg/ml. DNA concentrations greater than 200 μg/ml are saturating. Transient expression is about 40-fold greater with linearized DNA compared to supercoiled DNA. Because it would be logistically prohibitive to routinely use DNA at 200 μg/ml in electroporations, DNA is preferably used at 50–100 μg/ml.

All of the literature and other documents cited hereinabove are incorporated by reference herein.

The invention has been described with reference to various specific and preferred embodiments and techniques. However, it should be understood that many variations and modifications may be made while remaining within the spirit and scope of the invention.

What is claimed is:

1. A method for producing a transgenic *Zea mays* plant comprising:
    (a) incubating a population of cultured *Zea mays* cells with at least one pectin-degrading enzyme in an aqueous osmoticum so as to partially degrade the walls of said cells to yield a population of transformation-competent *Zea mays* cells;
    (b) electroporating the population of transformation-competent *Zea mays* cells in a buffered aqueous osmoticum comprising recombinant DNA to yield a population of transgenic *Zea mays* cells stably transformed with said DNA;
    (c) growing transgenic *Zea mays* callus tissue from said cells; and
    (d) regenerating a population of fertile transgenic *Zea mays* plants from said transgenic callus tissue; wherein said plants comprise said DNA which is heritable.

2. The method of claim 1, wherein the culture of *Zea mays* cells is derived from a culture of embryogenic *Zea mays* callus tissue.

3. The method of claim 1 wherein the culture of *Zea mays* cells is obtained by culturing immature embryos.

4. The methods of claim 1 where said pectin degrading enzyme comprises pectinase, endopectin lyase, endopolygalacturonase or mixtures thereof.

5. The method of claim 4 wherein about 300–500 units of enzymatic activity, measured as maceration activity, present in said aqueous osmoticum in step (a) per ml of packed *Zea mays* cells.

6. The method of claim 1 wherein said pectin-degrading enzyme is pectolyase.

7. The method of claim 4 wherein the aqueous osmoticum in step (a) further comprises cellulase, xylanase or mixtures thereof.

8. The method of claim 4 wherein the incubation is carried out for about 0.75–3.0 hours at about 20°–30° C.

9. The method of claim 1 wherein said osmoticum comprises a sugar or a ($C_2$–$C_6$) polyol.

10. The method of claim 9 wherein the osmoticum is glycerol, sucrose, sorbitol, mannitol, or mixtures thereof.

11. The method of claim 10 wherein the osmoticum comprises an about 0.3–0.5M solution of the sugar or the ($C_2$–$C_6$) polyol.

12. The method of claim 1 wherein the electroporation is carried out at a capacitor capacitance of about 140"250 μF, at about 70–140 V and about 280–560 v/cm.

13. The method of claim 1 wherein the pH of the aqueous osmoticum is about 7–7.7.

14. The method of claim 1 wherein the recombinant DNA is a linearized plasmid DNA.

15. The method of claim 14 wherein about 1-100 μg of recombinant DNA per 0.1 ml of packed *Zea mays* cells is present in step (b).

16. The method of claim 14 wherein the recombinant DNA comprises a selectable marker gene or a reporter gene.

17. The method of claim 16 wherein said selectable marker gene encodes resistance to hygromycin B.

18. The method of claim 16 wherein the reporter gene encodes β-glucuronidase.

19. The method of claim 1 wherein the recombinant DNA encodes a protein.

20. The method of claim 19 wherein the protein is a seed storage protein.

21. The method of claim 19 wherein the protein is an enzyme.

* * * * *

UNITED STATES PATENT AND TRADEMARK OFFICE
CERTIFICATE OF CORRECTION

PATENT NO. : 5,384,253

DATED : January 24, 1995

INVENTOR(S) : Richard A. Krzyzek et al.

It is certified that error appears in the above-identified patent and that said Letters Patent is hereby corrected as shown below:

In column 26, line 57 please delete "140"250" and insert --140-250--

In column 26, line 57 please delete "and about 280-560" and insert -- and at about 280-560--

Signed and Sealed this

Twenty-second Day of July, 1997

Attest:

BRUCE LEHMAN

Attesting Officer

Commissioner of Patents and Trademarks